United States Patent [19]

Regen

[11] Patent Number: 5,834,453
[45] Date of Patent: Nov. 10, 1998

[54] METHODS FOR THE MANUFACTURE AND USE OF ANTIMICROBIAL STEROL CONJUGATES

[75] Inventor: Steven L. Regen, Allentown, Pa.

[73] Assignee: Lehigh University, Bethlehem, Pa.

[21] Appl. No.: 877,618

[22] Filed: Jun. 17, 1997

Related U.S. Application Data

[63] Continuation of Ser. No. 711,161, Sep. 9, 1996, abandoned, which is a continuation-in-part of Ser. No. 452,846, May 30, 1995, Pat. No. 5,583,239.

[51] Int. Cl.$^6$ .................................................. A61K 31/56
[52] U.S. Cl. ........................................... 514/182; 514/169
[58] Field of Search ..................................... 514/169, 182

[56] References Cited

U.S. PATENT DOCUMENTS

| | | | |
|---|---|---|---|
| 5,122,520 | 6/1992 | Azria et al. | 514/171 |
| 5,352,682 | 10/1994 | Sipos | 514/182 |
| 5,583,239 | 12/1996 | Regen | 552/554 |

OTHER PUBLICATIONS

International Publication No. WO 95/29186; Compositions and methods for cell transformation; based upon International Patent Application No. PCT/US95/04806; Inventors: Kahne and Kahne; Applicant: The Trustees of Princeton University; Nov. 2, 1995.

*Primary Examiner*—Allen J. Robinson
*Assistant Examiner*—Barbara Badio
*Attorney, Agent, or Firm*—Yahwak & Associates

[57] ABSTRACT

A method of forming a pharmaceutical composition of antimicrobial sterol conjugates having the following formulae:

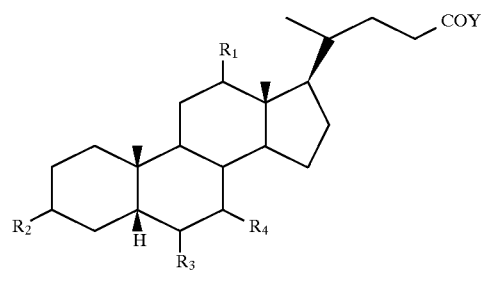

or

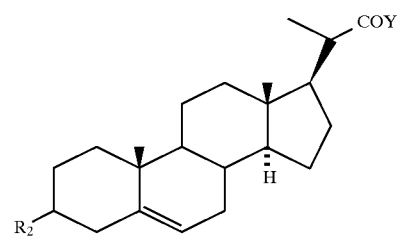

wherein $R_1$, $R_2$, $R_3$, $R_4$ and Y are as defined in the specification. Also disclosed is a method of inducing an antimicrobial effect by administrating these pharmaceutical compositions.

5 Claims, No Drawings

METHODS FOR THE MANUFACTURE AND USE OF ANTIMICROBIAL STEROL CONJUGATES

This is a continuation of application Ser. No. 08/711,161, filed Sep. 9, 1996, now abandoned, which is a continuation-in-part of application Ser. No. 08/452,846, filed May 30, 1995, now U.S. Pat. No. 5,583,239.

Partial financial support in the making of the invention described herein was provided by the National Institutes of Health. In view of providing financial support to the making of the invention described herein, the United States government has certain statutory interests in the invention under 35 USC 200 et seq.

The emergence of multi-drug resistant microorganisms, such as methicillin resistant *Staphylococcus aureus*, vancomycin resistant Enterococcus, and *Mycobacterium tuberculosis* is a most serious clinical problem. At the present, new classes of antimicrobial agents are needed in order to combat the clinical progression of such diseases.

In the course of studies exploring the diversity of antibiotics from animal sources, Michael Zasloff and his colleagues reported on the isolation, structural determination and antimicrobial activity of the first aminosterol antibiotic from stomach extract of the dogfish shark *Squalus acanthias* [see *Proc. Natl. Acad. Sci.*, USA 90:1354 (1993), and U.S. Pat. No. 5,192,756]. This antibiotic was given the name "squalamine" by its discoverers since it was derived from the genus Squalus, and its chemical structure was that of an amine. Since its discovery, this naturally-occurring aminosterol has attracted considerable interest because of its potent antimicrobial activity against a broad spectrum of microorganisms, however, the mechanism of antimicrobial action by squalamine (or the squalamine mimics according to the present invention) has yet to be elucidated.

Chemically, squalamine is 3β-N-1-{N-[3-(4-aminobutyl)]-1,3-diaminopropane}-7α,24ζ-dihydroxy-5α-cholestane 24-sulfate, and has the structure:

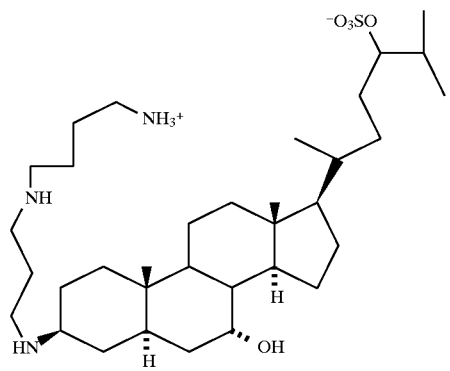

At the present, the feasibility of obtaining large quantities of this steroidal antibiotic from natural sources appears questionable since only trace amounts are present in the liver and gallbladder of the shark. While a recent synthesis [see Tetrahedron Letters 35(44):8103 (1994)] has confirmed the structure of squalamine, the 17 steps that are needed to achieve the product, together with a low overall yield (0.36%) and expensive starting material (3β-acetoxy-5-cholenic acid) makes such a route impractical for large-scale production.

Accordingly, there is a need to develop more economical procedures, both in time and cost, for the synthesis of squalamine, and that is where the research effort that led to the making of the compounds described for the first time herein, was directed. This research effort led to the discovery of two and three-step protocols that led to the synthesis of molecules generally sharing a sterol core similar to that of squalamine, but also share its extraordinary antimicrobial properties. Furthermore, the results obtained in the making of the present invention also demonstrate for the first time that the placement of a pendant polyamine (e.g., spermine) and sulfate groups on the A and D rings of a structurally related sterol may be reversed with retention of antimicrobial activity, and that much more accessible squalamine-like compounds, or "mimics", are possible.

By the term "mimic" as used in the description of the present invention is meant an aminosterol compound that contains a cholane ring core (which may be saturated or unsaturated) as found in squalamine. By the term "spermine" as used in the description of the present invention is meant an amino-organic radical having the chemical formula —NH(CH$_2$)$_3$NH(CH$_2$)$_4$NH(CH$_2$)$_3$NH$_2$.

Accordingly, it is one aspect of the present invention to describe a series of novel squalamine mimics having a pendant polyamine (e.g., spermine) attached to the D ring of the molecule, and a sulfate group attached to the A ring of the molecule.

It is another aspect of the present invention to describe a protocol by which such squalamine mimics may be synthesized.

It is still another aspect of the present invention to provide data showing that the squalamine mimics according to the present invention exhibit potent antibiotic properties against a broad spectrum of microorganisms.

These and other aspects of the present invention may be more fairly understood in conjunction with the following examples and detailed description of the present invention.

Synthesis for the compounds according to the present invention begins with one of seven starting materials, all of which are commercially available. These materials are 23, 24-bisnor-5-cholenic acid-3β-ol; deoxycholic acid; cholic acid; 5β-cholanic acid; 5β-cholanic acid-3α-ol; 5β-cholanic acid-3α,6α-diol; and 5β-cholanic acid-3α,7α-diol. Structurally these materials are:

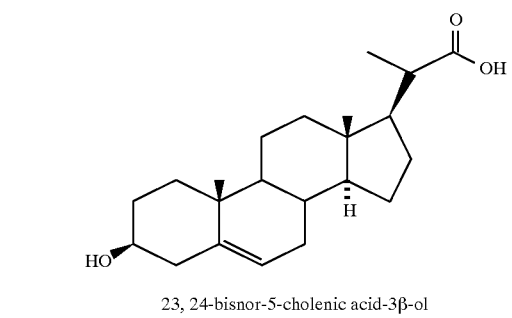

23, 24-bisnor-5-cholenic acid-3β-ol

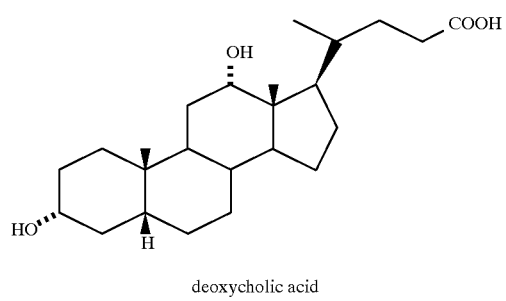

deoxycholic acid

-continued

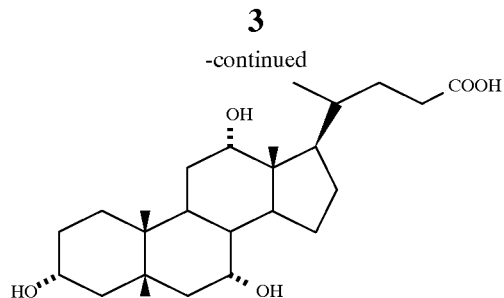

cholic acid

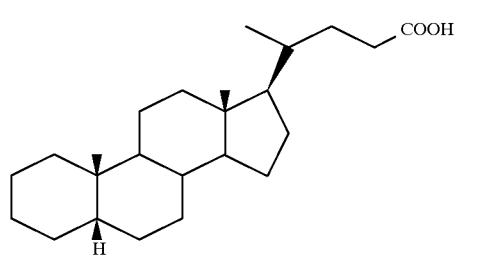

5β-cholanic acid

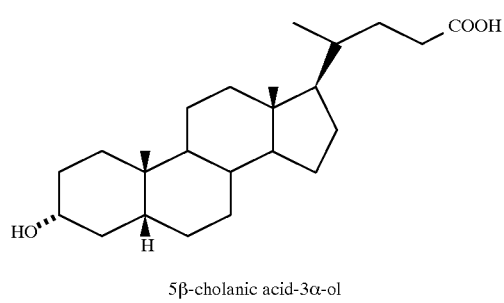

5β-cholanic acid-3α-ol

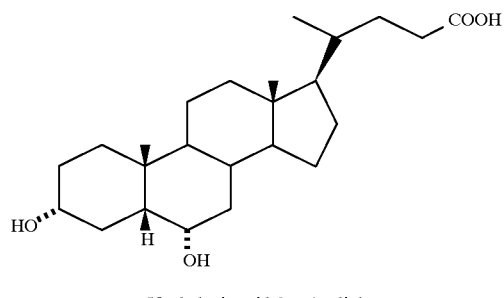

5β-cholanic acid-3α, 6α-diol

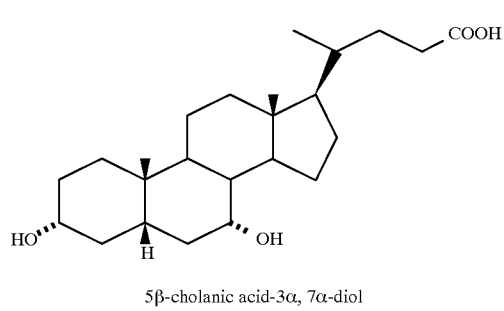

5β-cholanic acid-3α, 7α-diol

Using these materials in the appropriate protocol, compounds according to the present invention may be readily synthesized.

In its broadest interpretation, the compounds according to the present invention are those having the formulae

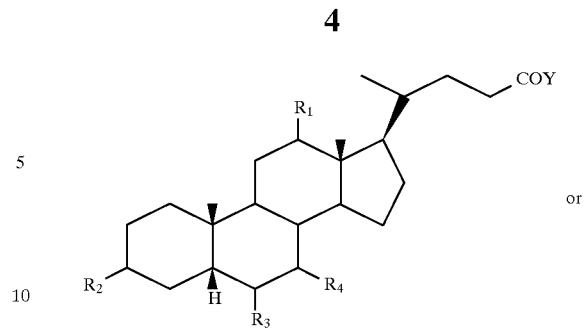

or

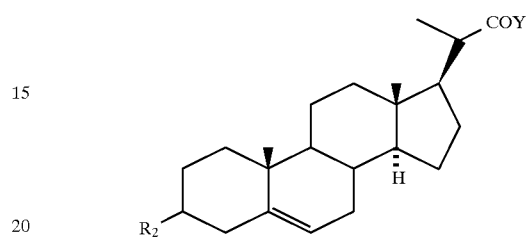

wherein each $R_1$, $R_2$, $R_3$, and $R_4$ may be H, OH or $OSO_3H$; and wherein Y is spermine, that is $NH(CH_2)_3NH(CH_2)_4NH(CH_2)_3NH_2$ (i.e., spermine); $NHCH_2CH_2CH_2CH_2NH_2$ (i.e., putrescine); or $NHCH_2CH_2NHCH_2CH_2NHCH_2CH_2NH_2$ (i.e., triethylenetetramine).

More specifically, the preferred compounds according to the present invention are those having the following structures:

The 23,24-Bisnor-5-cholenic acid-3-β-ol based squalamine mimics:

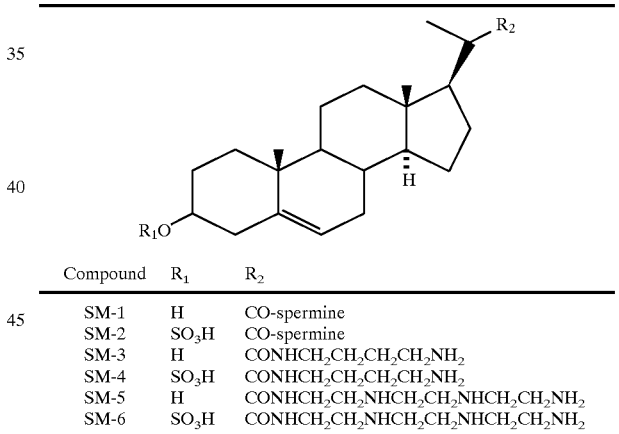

| Compound | $R_1$ | $R_2$ |
|---|---|---|
| SM-1 | H | CO-spermine |
| SM-2 | $SO_3H$ | CO-spermine |
| SM-3 | H | $CONHCH_2CH_2CH_2CH_2NH_2$ |
| SM-4 | $SO_3H$ | $CONHCH_2CH_2CH_2CH_2NH_2$ |
| SM-5 | H | $CONHCH_2CH_2NHCH_2CH_2NHCH_2CH_2NH_2$ |
| SM-6 | $SO_3H$ | $CONHCH_2CH_2NHCH_2CH_2NHCH_2CH_2NH_2$ |

The deoxycholic acid based squalamine mimics:

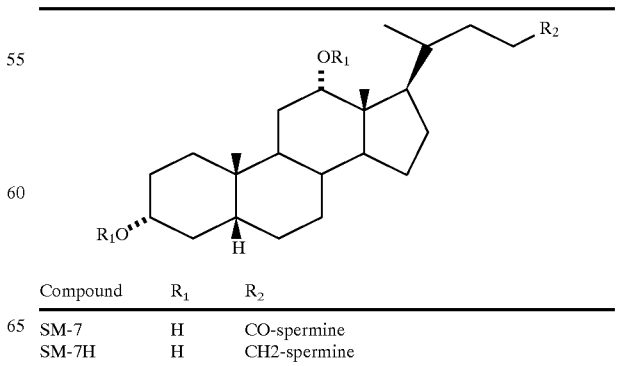

| Compound | $R_1$ | $R_2$ |
|---|---|---|
| SM-7 | H | CO-spermine |
| SM-7H | H | CH2-spermine |

-continued

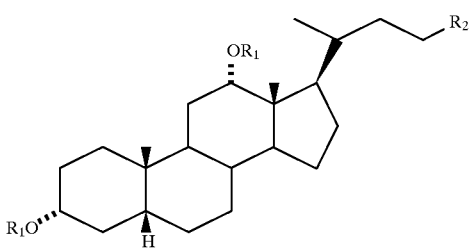

| Compound | R₁ | R₂ |
|---|---|---|
| SM-8 | SO₃H | CO-spermine |
| SM-9 | H | CONHCH₂CH₂CH₂CH₂NH₂ |
| SM-9H | H | CH₂NHCH₂CH₂CH₂CH₂NH₂ |
| SM-10 | SO₃H | CONHCH₂CH₂CH₂CH₂NH₂ |
| SM-10 | H | CONHCH₂CH₂NHCH₂CH₂NHCH₂CH₂NH₂ |
| SM-12 | SO₃H | CONHCH₂CH₂NHCH₂CH₂NHCH₂CH₂NH₂ |

The cholic acid based squalamine mimics:

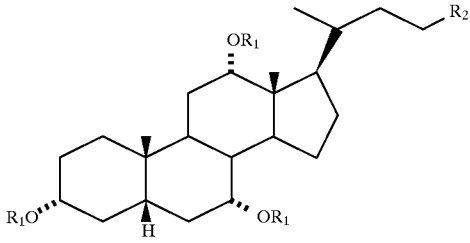

| Compound | R₁ | R₂ |
|---|---|---|
| SM-13 | H | CO-spermine |
| SM-14 | SO₃H | CO-spermine |
| SM-15 | H | CONHCH₂CH₂CH₂CH₂NH₂ |
| SM-16 | SO₃H | CONHCH₂CH₂CH₂CH₂NH₂ |
| SM-17 | H | CONHCH₂CH₂NHCH₂CH₂NHCH₂CH₂NH₂ |
| SM-18 | SO₃H | CONHCH₂CH₂NHCH₂CH₂NHCH₂CH₂NH₂ |

The ursocholanic acid based squalamine mimics:

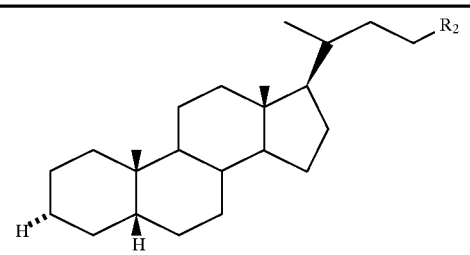

| Compound | R₂ |
|---|---|
| SM-19 | CO-spermine |
| SM-20 | CONHCH₂CH₂CH₂CH₂NH₂ |
| SM-21 | CONHCH₂CH₂NHCH₂CH₂NHCH₂CH₂NH₂ |

The lithocholic acid based squalamine mimics:

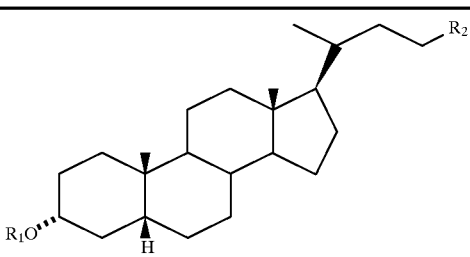

| Compound | R₁ | R₂ |
|---|---|---|
| SM-22 | SO₃H | CO-spermine |
| SM-23 | SO₃H | CONHCH₂CH₂CH₂CH₂NH₂ |
| SM-24 | SO₃H | CONHCH₂CH₂NHCH₂CH₂NHCH₂CH₂NH₂ |
| SM-25 | H | CO-spermine |
| SM-26 | H | CONHCH₂CH₂CH₂CH₂NH₂ |
| SM-27 | H | CONHCH₂CH₂NHCH₂CH₂NHCH₂CH₂NH₂ |

The hyodeoxycholic acid based squalamine mimics:

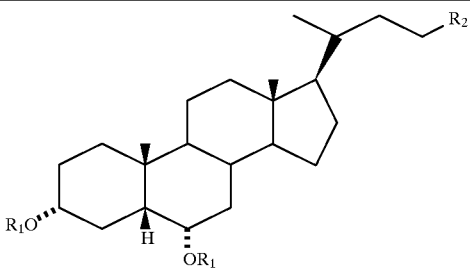

| Compound | R₁ | R₂ |
|---|---|---|
| SM-28 | H | CO-spermine |
| SM-29 | SO₃H | CO-spermine |
| SM-30 | H | CONHCH₂CH₂CH₂CH₂NH₂ |
| SM-31 | SO₃H | CONHCH₂CH₂CH₂CH₂NH₂ |
| SM-32 | H | CONHCH₂CH₂NHCH₂CH₂NHCH₂CH₂NH₂ |
| SM-33 | SO₃H | CONHCH₂CH₂NHCH₂CH₂NHCH₂CH₂NH₂ |

The chenodeoxycholic acid based squalamine mimics:

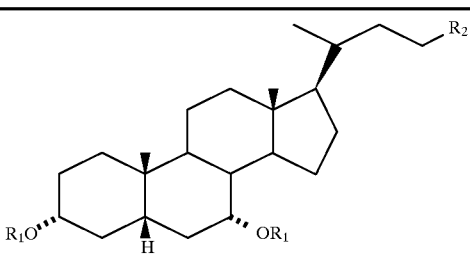

| Compound | R₁ | R₂ |
|---|---|---|
| SM-34 | H | CO-spermine |
| SM-35 | SO₃H | CO-spermine |
| SM-36 | H | CONHCH₂CH₂CH₂CH₂NH₂ |
| SM-37 | SO₃H | CONHCH₂CH₂CH₂CH₂NH₂ |
| SM-38 | H | CONHCH₂CH₂NHCH₂CH₂NHCH₂CH₂NH₂ |
| SM-39 | SO₃H | CONHCH₂CH₂NHCH₂CH₂NHCH₂CH₂NH₂ |

Individual compounds according to the present invention may be synthesized using the appropriate of three protocols. For example, Compounds such as 1 and 2 may be synthesized according to the following protocol using 23,24-bisnor-5-cholenic acid-3-β-ol as the starting material:

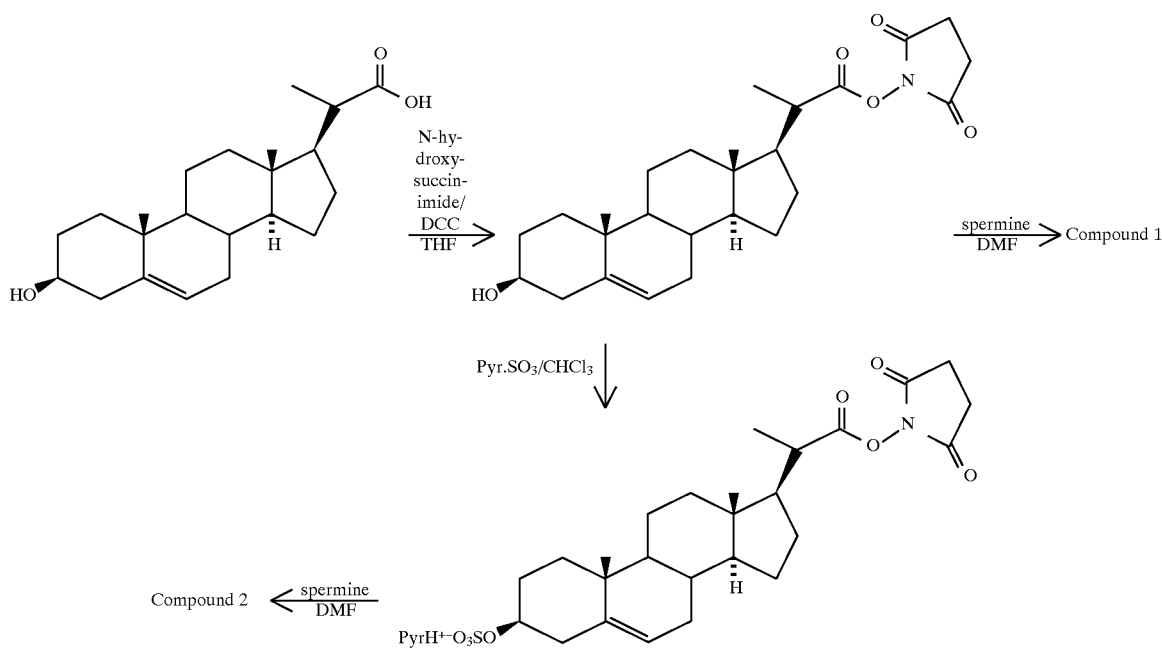

More specifically, compounds SM-1 and SM-2 were prepared according to the following examples.

EXAMPLE I

The 23,24-Bisnor-3β-ol-5-cholenic Acid N-Hydroxylsuccinimidyl ester shown in the above protocol was synthesized by adding, dropwise, a solution that was prepared from dicyclohexylcarbodiimide (419 mg, 2.04 mmol) plus 5 ml of tetrahydrofuran (THF) to a stirred mixture of 23, 24-bisnor-5-cholenic acid-3β-ol (702 mg, 2.03 mmol) and N-hydroxysuccinimide (235 mg, 2.0 mmol) that was suspended in 30 ml of anhydrous THF maintained at 50° C. The reaction mixture was stirred for an additional 3 hours at 50° C., and left overnight at ambient temperature. The supernatant was separated from the product mixture by filtration and concentrated under reduced pressure. The solid residue that resulted was then dissolved in 40 ml of chloroform and washed, sequentially, with saturated sodium bicarbonate (20 ml), water (20 ml), and brine (10 ml). The chloroform solution was then dried over anhydrous sodium sulfate and concentrated under reduced pressure. Recrystallization from acetone/petroleum ether gave 577 mg (64%) of 23,24-bisnor-3β-ol-5-cholenic acid N-hydrosylsuccinimidyl ester as a colorless powder, having a melting point of 214°–216° C.

Compound SM-1, the 23,24-Bisnor-3β-ol-5-cholenic acid 3-ol spermine conjugate, was prepared according to the following example II.

EXAMPLE II

To a stirred solution of spermine (68 mg, 0.34 mmol) in 1 ml of anhydrous chloroform was added, dropwise, a solution prepared from 23,24-bisnor-3β-ol-cholenic acid N-hydroxylsuccinimidyl ester (86 mg, 0.19 mmol) plus 4 ml of chloroform over a 5 minute period at ambient temperature. After 30 minutes of reaction, some precipitate appeared in the flask. The heterogenous mixture was stirred overnight, and then transferred to a test tube and washed, sequentially, with 0.1M NaOH (1×2 ml), water (1×2 ml), and saturated sodium chloride (1×1 ml). After drying over anhydrous potassium carbonate and subsequent solvent removal under reduced pressure, 84 mg of crude product was obtained. Subsequent chromatographic purification using 3.0 g of EM Science silica gel, eluting first with $CH_3OH$ and then with $CH_3OH/30\%$ $NH_4OH$ (4/1, v/v), afforded 42 mg of pure product.

Pyridium 23,24-bisnor-3β-ol-5-cholenic Acid N-hydroxysuccinimidyl ester 3-sulfate was prepared according to the following example.

EXAMPLE III

To a solution of 23,24-bisnor-3β-ol-5-cholenic acid N-hydrosylsuccinimidyl ester (445 mg, 1.00 mmol) in 20 ml of anhydrous chloroform was added, in a single portion, 481 mg (3.03 mmol) of sulfur trioxide/pyridine complex. After stirring the heterogenous mixture for 14 hours at ambient temperature, an additional 20 ml of chloroform was then added, and the mixture cooled to about −10° C., and filtered. Concentration of the filtrate under reduced pressure, followed by recrystallization from acetone/petroleum ether, afforded 355 mg (75%) of Pyridium 23,24-bisnor-3β-ol-5-cholenic Acid N-hydroxysuccinimidyl ester 3-sulfate as colorless crystals having a melting point of 220°–224° C. (dec).

Compound SM-2, the 23,24-bisnor-3β-ol-5-cholenic acid 3-sulfate spermine conjugate was prepared according to the following example.

EXAMPLE IV

To a stirred solution of spermine (215 mg, 1.06 mmol) in 15 ml of anhydrous DMF, which was maintained at 0° C., was added a solution of pyridinium 23,24-bisnor-3β-ol-5-cholenic acid N-hydroxysuccinimidyl ester 3-sulfate (380 mg, 0.63 mmol) in 2.5 ml of anhydrous DMF over a 20 minute period. The mixture was then stirred at ambient temperature for 1 hour, quenched with 20 ml of 0.1M NaOH, and extracted with 1-butanol (2×20 ml). The combined extracts were washed with water (3×20 ml) and brine (2×20 ml) and dried over sodium sulfate. Removal of solvent under reduced pressure (45° C.) afforded 218 mg of solid residue, which was then purified by column chromatography (4.5 g EM Science silica gel, CH$_3$OH/30% NH$_4$OH (4/1, v/v)), and filtration (0.45 μm Millipore) to give 140 mg (35%) of compound 2 as a cream-colored solid having a melting point of 212–221 (dec).

Compounds such as compound SM-7 may be synthesized according to the following protocol using deoxycholic acid as the starting material:

in the form of a colorless powder, and having a melting point of 167°–169° C.

Compound SM-7, the deoxycholic acid-spermine conjugate was synthesized according to the following example.

EXAMPLE VI

To a stirred solution of spermine (241 mg, 1.19 mmol) in 4 ml of anhydrous CH$_2$Cl$_2$ was added, over the course of 5 minutes at ambient temperature, a solution that was prepared from the N-hydroxylsuccinimidyl ester of deoxycholic acid

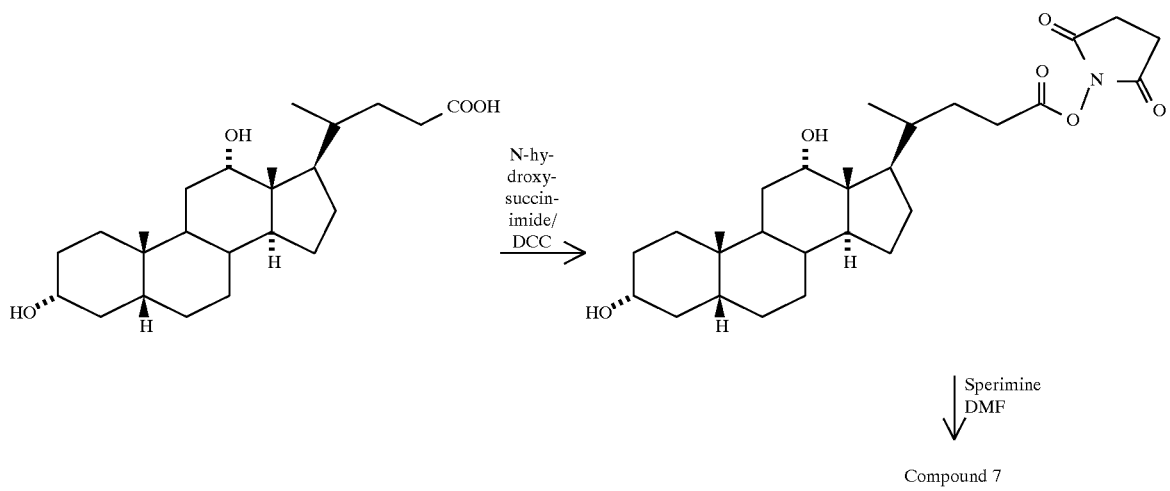

Compound 7

The N-hydroxylsuccinimidyl ester of deoxycholic acid used in the synthesis of compound SM-7 was prepared in accordance with the following example.

EXAMPLE V

Deoxycholic acid (7.86 g, 20.0 mmol) and N-hydroxysuccinimide (2.38 g, 20.7 mmol) were partially dissolved in 100 ml of anhydrous tetrahydrofuran and then added to a stirred solution that was prepared from dicyclohexylcarbodiimide (4.80 g, 23.3 mmol) plus 20 ml of tetrahydrofuran.

The reaction mixture was stirred for an additional 3.5 hours and the dicyclohexyl urea removed by filtration. After the dicyclohexyl urea was washed with tetrahydrofuran, the combined filtrate was concentrated under reduced pressure to about one-third of its initial volume. Chloroform (150 ml) was then added, and the resulting solution was washed with saturated aqueous sodium bicarbonate (2×100 ml), water (1×100 ml), and saturated sodium chloride (1×50 ml). After drying with anhydrous sodium sulfate, the solvent was removed under reduced pressure, and the residue was recrystallized from ethyl acetate/hexanes to give 7.08 g of product (351 mg, 0.71 mmol) 4 ml of CH$_2$Cl$_2$, and 2 ml of tetrahydrofuran. During this addition, a colorless precipitate appeared, and an additional 4 ml of anhydrous chloroform was added to the reaction mixture.

The heterogenous mixture was stirred at ambient temperature overnight, and the solvent was then removed under reduced pressure. The residue was then dissolved in 8 ml of chloroform. The resulting solution was placed in 2 test tubes and these were washed with 0.1M NaOH (1×2 ml), water (1×2 ml), and saturated sodium chloride (1 ml). In order to assist phase separation, the mixtures were subjected to centrifugation. The resulting organic phase was then dried over anhydrous potassium carbonate and concentrated under reduced pressure to give 320 mg of solid residue. Subsequent chromatography (5 g of EM Silica gel), using CH$_3$OH/30% NH$_4$OH (3/2, v/v) as he eluent afforded 255 mg of product which was solidified on drying.

Compounds such as compound SM-13 may be synthesized according to the following protocol using cholic acid as the starting material:

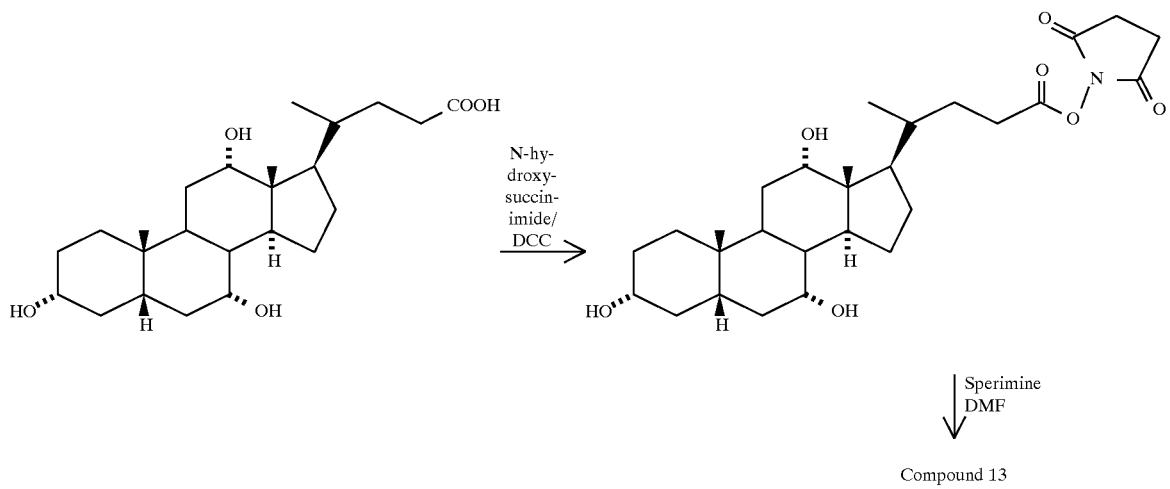

Compound 13

The N-hydroxylsuccinimidyl ester of cholic acid used as the intermediate in the preparation of compound SM-13 was synthesized according to the following example.

EXAMPLE VII

To a stirred solution prepared from cholic acid (8.18 g, 20.0 mmol) and N-hydroxysuccinimide (2.7 g, 23.5 mmol) in 80 ml of anhydrous tetrahydrofuran was added a solution that was prepared from dicyclohexylcarbodiimide (4.22 g, 20.5 mmol) and 20 ml of tetrahydrofuran. The mixture was stirred at ambient temperature for 3 hours, and then allowed to stand overnight. The resultant supernatant was concentrated under reduced pressure, and the residue dissolved in 200 ml of chloroform. The solution was then washed with saturated sodium carbonate (2×200ml), water (1×100 ml), and saturated sodium chloride (1×50 ml). After drying with anhydrous sodium sulfate and solvent removal under reduced pressure, 9.1 g of crude product was obtained which was used without further purification.

Compound SM-13, the cholic acid-spermine conjugate was synthesized according to the following example,

EXAMPLE VIII

To a stirred solution of spermine (196 mg, 0.97 mmol) in 2 ml of anhydrous chloroform was added, over the course of 5 minutes at ambient temperature, a solution prepared from the N-hydroxylsuccinimidyl ester of cholic acid (402 mg, 0.59 mmol) plus 4 ml of chloroform. The homogeneous mixture was then stirred overnight, transferred to two test tubes, and washed with 0.1M NaOH (1×2 ml), water (1×2 ml), and saturated sodium chloride (1 ml). After drying with anhydrous potassium carbonate, the solvent was removed under reduced pressure to give 88 mg of crude product. Subsequent purification using 2.0 g of silica, and $CH_3OH$/30% $NH_4OH$ (3/2, v/v) as the eluting solvent, afforded 55 mg of the desired conjugate in the form of a colorless, foam-like solid.

The remainder of the compounds according to the present invention may be synthesized using similar protocols with the appropriate starting material having the similar steroidal structure as found in the desired end-product compound.

The antimicrobial activity of the compounds according to the present invention were compared with the results obtained for squalamine as reported in Proc. Nat. Acad. Sci. USA 90:1354 (1993), supra, the disclosure of which is incorporated in toto herein. The data reported in the following table is the minimum inhibitory concentration (MIC) required for complete inhibition of microbial growth. The MIC was determined utilizing known micro-broth dilution methods in which inocula of $10^6$/ml of the test organism were incubated in 0.5× trypticase soy broth at 35° C. for 24 hours. MIC's were also tested under various pH conditions, with calcium chloride or magnesium chloride, or with immobilized horse serum.

Hemolytic activity of the squalamine mimics according to the present invention were also studied by incubating sheep red blood cells for 24 hours at 37° C. in saline (final concentration of 0.5%) with or without respective concentrations of the squalamine mimics. The minimal hemolytic concentration (MHC) was determined as the lowest concentration of a mimic that raised visible hemolysis.

The MIC assay data reported in the following table is considered by scientists, especially when combined with the results of the MHC assay, to be an accurate indication for the therapeutic potential of compounds tested when used to treat microbial diseases in animals, particularly in mammals.

| | ANTIMICROBIAL ACTIVITY (MIC) ($\mu$g/ml) | | | | | | | | | |
|---|---|---|---|---|---|---|---|---|---|---|
| ORGANISMS | SM-1 | SM-2 | SM-5 | SM-7 | SM-7H | SM-8 | SM-9 | SM-9H | SM-11 | SM-13 |
| Gram positive cocci: | | | | | | | | | | |
| E. faecalis (29212) | ND[a] | >100 | >100 | 3.13 | 6.25 | >100 | 25 | 6.25 | 12.5 | 50 |
| E. faecium (T6480-9) | ND | >100 | >100 | 6.25 | 6.25 | 100 | 50 | 25 | 12.5 | 50 |
| S. aureus (25923) | 3.13 | 12.5 | 50 | 1.56 | 0.78 | 25 | 25 | 1.56 | 6.25 | 6.25 |

-continued

| ORGANISMS | ANTIMICROBIAL ACTIVITY (MIC) (μg/ml) | | | | | | | | | |
|---|---|---|---|---|---|---|---|---|---|---|
| | SM-1 | SM-2 | SM-5 | SM-7 | SM-7H | SM-8 | SM-9 | SM-9H | SM-11 | SM-13 |
| S. aureus (29213) | 6.25 | >100 | 100 | 1.56 | 0.78 | 25 | 25 | 1.56 | 12.5 | 12.5 |
| S. aureus (H20809) | ND | ND | >100 | 1.56 | 0.78 | 25 | 25 | 3.13 | 12.5 | 6.25 |
| S. epidermidis (12228) | 1.56 | 3.13 | 25 | 0.78 | 0.39 | 25 | 25 | 1.56 | 6.25 | 3.13 |
| S. agalactiae (13813) | ND | >100 | >100 | 3.13 | 0.78 | 50 | 12.5 | 3.13 | 6.25 | 12.5 |
| S. pneumoniae (6305) | ND | >100 | >100 | 3.13 | 1.56 | 50 | 25 | 6.25 | 12.5 | 25 |
| S. pyrogenes (19615) | ND | 6.25 | 6.25 | 0.78 | 0.39 | 6.25 | 6.25 | 0.78 | 6.25 | 3.13 |
| Gram negative rods: | | | | | | | | | | |
| E. cloacae (13047) | ND | >100 | >100 | 12.5 | 12.5 | >100 | 50 | 100 | 12.5 | >100 |
| E. coli (25922) | 12.5 | 6.25 | 100 | 3.13 | 6.25 | >100 | 50 | 25 | 12.5 | 25 |
| K. pneumoniae (13883) | ND | 12.5 | >100 | 3.13 | 12.5 | 50 | 50 | 50 | 12.5 | >100 |
| P. vulgaris (13315) | 25 | >100 | >100 | 3.13 | 6.25 | 50 | 50 | 12.5 | 25 | >100 |
| P. aeruginosa (10145) | ND | 12.5 | 25 | 6.25 | 3.13 | 100 | 100 | 12.5 | 6.25 | 25 |
| P. aeruginosa (2853) | 1.56 | 3.13 | 25 | 3.13 | 3.13 | 25 | 100 | 6.25 | 6.25 | 25 |
| S. marcescens (13880) | >100 | >100 | >100 | 25 | 12.5 | >100 | >100 | >100 | 50 | >100 |

20

| ORGANISMS | ANTIMICROBIAL ACTIVITY (MIC) (μg/ml) | | | | | | | | |
|---|---|---|---|---|---|---|---|---|---|
| | SM-17 | SM-19 | SM-21 | SM-22 | SM-25 | SM-27 | SM-28 | SM-32 | SM-34 | SM-35 |
| Gram positive cocci: | | | | | | | | | | |
| E. faecalis (29212) | 50 | 6.25 | 3.13 | >100 | 3.13 | 12.5 | 50 | 100 | 3.13 | 6.25 |
| E. faecium (T6480-9) | 50 | 3.13 | 1.56 | >100 | 3.13 | 12.5 | 50 | 100 | 6.25 | 6.25 |
| S. aureus (25923) | 25 | 3.13 | 3.13 | 1.56 | 0.78 | 6.25 | 6.25 | 25 | 0.78 | 6.25 |
| S. aureus (29213) | 25 | 3.13 | 3.13 | 1.56 | 0.78 | 6.25 | 6.25 | 25 | 1.56 | 6.25 |
| S. aureus (H20809) | 50 | 3.13 | 3.13 | 3.13 | 0.39 | 6.25 | 6.25 | 25 | 1.56 | 8.25 |
| S. epidermidis (12228) | 25 | 1.56 | 1.56 | 1.56 | 0.39 | 3.13 | 3.13 | 25 | 0.78 | 3.13 |
| S. agalactiae (13813) | 12.5 | 3.13 | 1.56 | >100 | 0.78 | 3.13 | 12.5 | 25 | 1.56 | 6.25 |
| S. pneumoniae (6305) | 25 | 0.78 | 1.56 | 25 | 3.13 | 3.13 | 50 | 25 | 3.13 | 3.13 |
| S. pyrogenes (19615) | 12.5 | 3.13 | 3.13 | 1.56 | 0.78 | 1.56 | 1.56 | 12.5 | 0.78 | 3.13 |
| Gram negative rods: | | | | | | | | | | |
| E. cloacae (13047) | 50 | >100 | >100 | >100 | >100 | 25 | >100 | >100 | 12.5 | 12.5 |
| E. coli (25922) | 50 | 3.13 | 50 | >100 | 1.56 | 3.13 | 50 | 25 | 3.13 | 6.25 |
| K. pneumoniae (13883) | 50 | 6.25 | >100 | >100 | >100 | 6.25 | >100 | 50 | 8.25 | 12.5 |
| P. vulgaris (13315) | 50 | >100 | 50 | >100 | 12.5 | 12.5 | 50 | 50 | 12.5 | 25 |
| P. aeruginosa (10145) | 100 | >100 | 25 | >100 | 3.13 | 25 | 25 | 50 | 25 | 25 |
| P. aeruginosa (2853) | 50 | 12.5 | 25 | >100 | 0.78 | 12.5. | 25 | 25 | 12.5 | 12.5 |
| S. marcescens (13880) | >100 | >100 | >100 | >100 | >100 | 12.5 | >100 | >100 | 12.5 | >100 |

| ORGANISMS | ANTIMICROBIAL ACTIVITY (MIC) (μg/ml) | | | | | | | | | |
|---|---|---|---|---|---|---|---|---|---|---|
| | SM-1 | SM-2 | SM-5 | SM-7 | SM-7H | SM-8 | SM-9 | SM-9H | SM-11 | SM-13 |
| Fungi: | | | | | | | | | | |
| C. albicans (90028) | 100 | 12.5 | >100 | 3.13 | 6.25 | 100 | 25 | 3.13 | 12.5 | 12.5 |
| C. neofarmans (M68979) | 6.25 | 3.13 | >100 | 1.56 | 0.39 | 50 | 25 | 0.78 | 6.25 | 3.13 |
| C. neofarmans (90012) | ND | ND | >100 | 0.78 | 0.39 | 50 | 25 | 0.78 | 6.25 | ND |
| A. fumigatus (H1120) | ND | 12.5 | >100 | 12.5 | 12.5 | >100 | 50 | 12.5 | 12.5 | 25 |
| A. fumigatus (H29709) | ND | ND | >100 | 12.5 | 12.5 | >100 | 50 | 6.25 | 12.5 | ND |
| MHC (μg/ml) | 100 | >100 | >100 | 12.5 | 50 | >100 | 50 | 50 | 25 | >100 |

| ANTIMICROBIAL ACTIVITY (MIC) (µg/ml) | | | | | | | | | | |
|---|---|---|---|---|---|---|---|---|---|---|
| ORGANISMS | SM-17 | SM-19 | SM-21 | SM-22 | SM-25 | SM-27 | SM-28 | SM-32 | SM-34 | SM-35 |
| Fungi: | | | | | | | | | | |
| C. albicans (90028) | 25 | 3.13 | 6.25 | >100 | 3.13 | 25 | 6.25 | 25 | 3.13 | 25 |
| C. neoformans (M68979) | 12.5 | 0.78 | 1.56 | 25 | 0.39 | 3.13 | 3.13 | 25 | 3.13 | 12.5 |
| C. neoformans (90012) | 12.5 | 0.78 | 1.56 | 25 | 0.39 | 3.13 | 3.13 | 25 | 0.78 | 12.5 |
| A. fumigatus (H1120) | 25 | 3.13 | 6.25 | >100 | 12.5 | 100 | 25 | 50 | 12.5 | 25 |
| A. fumigatus (H29709) | 25 | 3.13 | 3.13 | >100 | 12.5 | 100 | 25 | 50 | 12.5 | 25 |
| MHC (µg/ml) | >100 | 6.25 | 3.13 | >100 | 50 | 50 | >100 | >100 | 25 | 6.25 |

The numbers in parentheses contained in the table correspond to accession numbers with the American Type Culture Collection (reference strains were either obtained from the American Type Culture Collection or from the Microbiology Laboratory at Memorial Sloan-Kettering Cancer Center; Bacterial strains were maintained on Columbia 5% sheep blood agar plates, and fungi were maintained on Sabouraud Dextrose agar plates). In addition to the results reported in the table, compound SM-2 was also tested against clinical isolates of *Cryptococcus neoformans* and *Aspergillus fumigatus* and gave MIC values of 3.13 and 12.5 µg/ml, respectively.

As evidenced by the data in the above table, the compounds according to the present invention exhibit potent antimicrobial activity against a broad spectrum of microorganisms.

In addition to the above summarized results, the squalamine mimics according to the present invention showed activity against gram negative rods, gram positive cocci including methicillin-resistant *Staphylococcus aureus*, vancomycin-resistant *Enterococcus faecium*, and fungi. The antibacterial action of SM-7, one of the most effective antimicrobial squalamine mimics according to the present invention, was bactericidal against *Escherichia coli*, *Pseudomonas aeruginosa*, and *Staphylococcus aureus* in a dose dependent manner. Subinhibitory concentrations of SM-7 markedly enhanced the antimicrobial activity of rifampin against gram negative rods. These results suggest that the mimics according to the present invention can disrupt an outer membrane of gram negative rods.

All of the squalamine mimics according to the present invention exhibited activity against the various groups of microorganisms tested. However, the MICs of SM-3, SM-4, and SM-14 were greater than 100 µg/ml, while those of SM-15 were 50 µm/ml or greater. No direct comparison of the squalamine mimics were made with squalamine because of the difficulty in obtaining an authentic sample of squalamine. However, the activities of some squalamine mimics exceeded those of squalamine as it has been reported in the literature, and extended to even vancomycin-resistant *E. faecium* and methicillin-resistant *S. aureus*. For example, the MICs of squalamine against *S. aureus* ATCC 29213, *P. vulgaris* ATCC 13883, and *P. aeruginosa* ATCC 27853 were 1-2, 4-8, and 4-8 µg/ml, respectively. The MICs of SM-7H and SM-25 against *S. aureus* ATCC 29213 were 0.78 µg/ml and those of SM-1 and SM-25 against *P. aeruginosa* ATCC 27853 were 1.56 and 0.78 µm/ml, respectively. The MIC of SM-7 against *P. vulgaris* ATCC 13883 was 3.13 µ/ml. Moreover, the activity of some squalamine mimics according to the present invention such as SM-7, SM-7H SM-11, SM-27 and SM-34 was found even against *S. marcescens*, a bacteria that is known to be resistant to squalamine. In general terms, as shown in the above table, SM-7 showed the most potent activity against gram negative rods of all the mimics tested; SM-25 showed the most potent activity against gram positive cocci and fungi of all the mimics tested.

Generally, spermine was found to be the most effective polyamine side chain among the compounds with the same steroidal backbone, and among the compounds with spermine, SM-7, SM-19, SM-25 and SM-34, based on deoxycholic, ursocholanic, lithocholic, and chenodeoxycholic acid, respectively, were highly active, while SM-13 and SM-28, based on cholic acid and hyodeoxycholic acid had lesser activity. SM-7, SM-13 and SM-25 that substituted their C-3 position to the non-sulfate residue were found to have more activity than SM-8, SM-14, and SM-22 in which the C-3 position was sulfated.

In summary, the squalamine mimics according to the present invention show broad antimicrobial properties; and several have greater activity and a wider spectrum of activity than squalamine. For example, SM-7, SM-7H, SM-11, SM-27 and SM-34 were effective against *S. marcescens*, a species resistant to squalamine. Moreover, many of the mimics according to the present invention had what would be considered to be significant antimicrobial activity, but no hemolytic activity. Recently [see MacDonald, D., et al., Program Abstracts, 35th Interscience Conference on Antimicrobial Agents Chemother., abstract No. F7 (1995)] squalamine has been suggested as a topical therapy for use in the prevention of sexually transmitted diseases such as HIV, herpes simplex, and *Neisseria gonorrhea* infection. The squalamine mimics, because of their broader and more active antimicrobial spectrum measured by both MIC and MHC assays as described above when compared to squalamine, may also be used as a more effective topical therapy for such sexually transmitted diseases as well as a more general antibiotic.

Although squalamine mimics according to the present invention may be administered intravenously, there is a significant loss of activity of some of the squalamine mimics in the presence of albumin, for example the bactericidal action of 12.5 µg/ml of SM-7 is completely inhibited by 40 mg/ml of bovine serum albumin; similarly, the most active squalamine mimics according to the present invention, i.e., SM-7, SM-7H, SM-25 and SM-34 demonstrate an unwanted hemolytic activity which precludes their use for intravenous administration. Accordingly, it is preferred, until such time as these adverse properties can be addressed and overcome, that the squalamine mimics according to the present invention be limited to topical applications.

The compounds according to the present invention, based upon the scientifically recognized correlation between the assays reported in the above table, and the therapeutic activity that can be expected when these compounds are topically administered to mammals, are potentially useful in the prevention and treatment of microbial disease states in mammals when topically administered to the mammal in amounts of from about 1 μg to about 100 mg per dosage (since preferred administration is by topical application, a 'dosage' would be the average amount of squalamine mimic contained in the topical cream, salve, ointment, etc. administered). Of course, the exact dose levels given on a daily basis is meant to be adapted by the physician to provide the optimum preventative or therapeutic response. For example, several divided doses may be administered daily, or the dose may be proportionally increased or reduced as indicated by the exigencies of the individual situation. The squalamine mimics according to the present invention may be administered as the free compound, or as a pharmaceutically acceptable salt thereof, or as an active agent in a pharmaceutical formulation that includes such carriers, fillers, extenders, dispersants, creams, gels and solutions as is common in the pharmaceutical formulatory arts. While the squalamine mimics according to the present invention may be formulated for various modes of application including, for example, modes that encompass topical, intravenous, oral, intraperitoneal, subcutaneous, vaginal, ocular or intramuscular routes of administration, because of the preference for topical administration (which also includes vaginal, ocular, intranasal routes in addition to applications to the skin or dermis). These preferred modes may be, for example, in the form of gels, creams, ointments, suppositories, or liquids. In addition the compounds according to the present invention may be compounded with other medicaments, or used in conjunction with devices such as, for example, condoms for use in vaginal application.

Thus while I have illustrated and described the preferred embodiment of my invention, it is to be understood that this invention is capable of variation and modification, and I therefore do not wish to be limited to the precise terms set forth, but desire to avail myself of such changes and alterations which may be made for adapting the invention to various usages and conditions. Thus, such variations and modifications are properly intended to be within the full range of equivalents, and therefore within the purview of the following claims.

Having thus described my invention and the manner and a process of making and using it in such full, clear, concise and exact terms so as to enable any person skilled in the art to which it pertains, or with which it is most nearly connected, to make and use the same;

I claim:

1. A method for the manufacture of a topical pharmaceutically active antimicrobial composition which comprises admixing a sterol conjugate compound of the formula

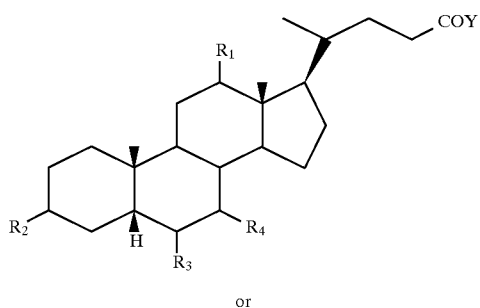

or

-continued

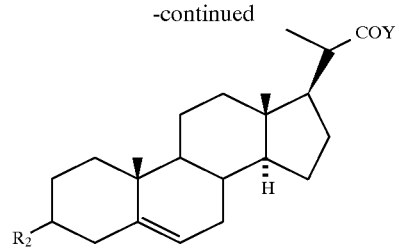

wherein each $R_1$, $R_2$, $R_3$ and $R_4$ is individually selected from the group consisting of H, OH and $OSO_3H$; and wherein Y is $NH(CH_2)_3NH(CH_2)_4NH(CH_2)_3NH_2$, $NHCH_2CH_2CH_2CH_2NH_2$, or $NHCH_2CH_2NHCH_2CH_2NHCH_2CH_2NH_2$ together with a pharmaceutically acceptable carrier for topical administration, said conjugate compound being in a sufficient concentration as to provide an antimicrobial dose of from 1 μg to 100 mg of said conjugate compound.

2. A method according to claim 1 wherein the resulting antimicrobial composition is a gel, ointment, solution, or salve.

3. A method for bringing about an antimicrobial effect in a mammal which comprises administering to said mammal by topical means an antimicrobial composition which comprises an active agent consisting of a sterol conjugate compound of the formula

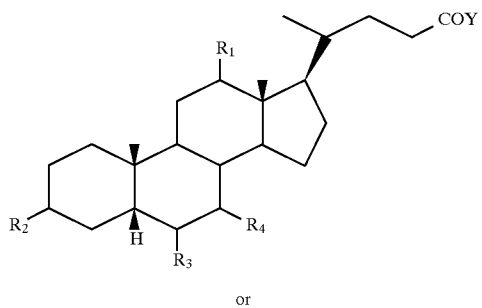

or

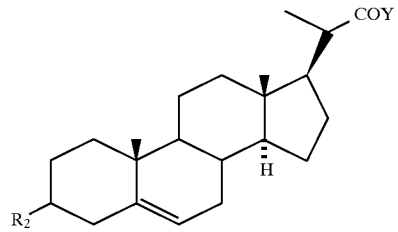

wherein each $R_1$, $R_2$, $R_3$ and $R_4$ is individually selected from the group consisting of H, OH and $OSO_3H$; and wherein Y is $NH(CH_2)_3NH(CH_2)_4NH(CH_2)_3NH_2$, $NHCH_2CH_2CH_2CH_2NH_2$, or $NHCH_2CH_2NHCH_2CH_2NHCH_2CH_2NH_2$ in admixture with a pharmaceutically acceptable carrier suitable for topical administration, said agent being present in a sufficient amount to bring about the antimicrobial effect.

4. A method to bring about an antimicrobial effect in a mammal which comprises administering to said mammal by topical means an antimicrobial composition which comprises a pharmaceutically-active sterol conjugate compound of a formula selected from the group consisting of (A)

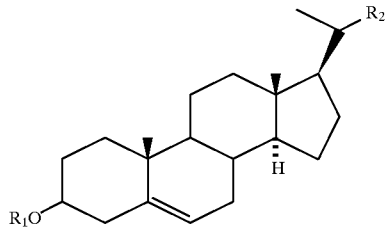

wherein $R_1$ is from the group H or $SO_3H$, and wherein $R_2$ is from the group CO-spermine, $CONHCH_2CH_2CH_2CH_2NH_2$, and $CONHCH_2CH_2NHCH_2CH_2NHCH_2CH_2NH_2$; (B)

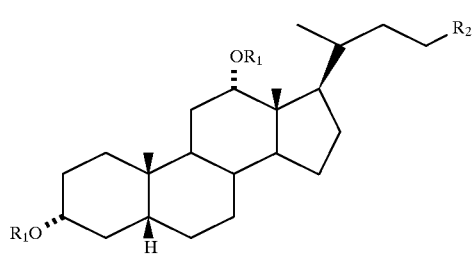

wherein $R_1$ is from the group H or $SO_3H$, and wherein $R_2$ is from the group CO-spermine, $CONHCH_2CH_2CH_2CH_2NH_2$, and $CONHCH_2CH_2NHCH_2CH_2NHCH_2CH_2NH_2$; (C)

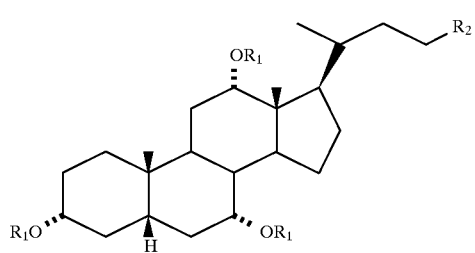

wherein $R_1$ is from the group H or $SO_3H$, and wherein $R_2$ is from the group CO-spermine, $CONHCH_2CH_2CH_2CH_2NH_2$, and $CONHCH_2CH_2NHCH_2CH_2NHCH_2CH_2NH_2$; (D)

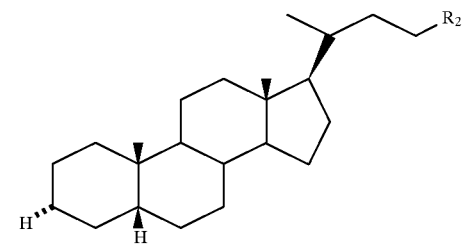

wherein $R_2$ is from the group CO-spermine, $CONHCH_2CH_2CH_2CH_2NH_2$, and $CONHCH_2CH_2NHCH_2CH_2NHCH_2CH_2NH_2$; (E)

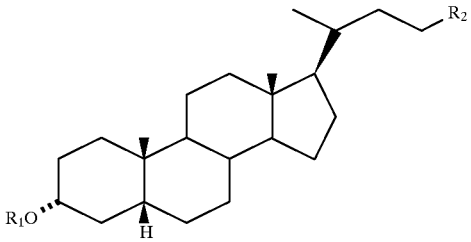

wherein $R_1$ is from the group H or $SO_3H$, and wherein $R_2$ is from the group CO-spermine, $CONHCH_2CH_2CH_2CH_2NH_2$, and $CONHCH_2CH_2NHCH_2CH_2NHCH_2CH_2NH_2$; (F)

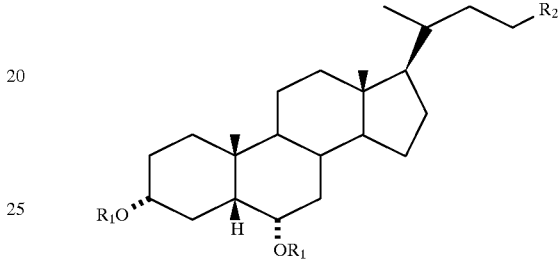

wherein $R_1$ is from the group H or $SO_3H$, and wherein $R_2$ is from the group CO-spermine, $CONHCH_2CH_2CH_2CH_2NH_2$, and $CONHCH_2CH_2NHCH_2CH_2NHCH_2CH_2NH_2$; and (G)

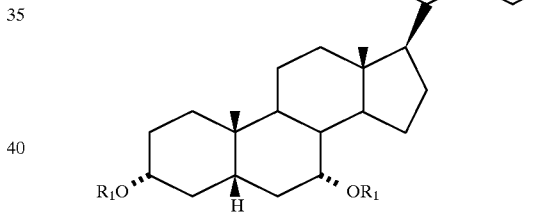

wherein $R_1$ is from the group H or $SO_3H$, and wherein $R_2$ is from the group CO-spermine, $CONHCH_2CH_2CH_2CH_2NH_2$, and $CONHCH_2CH_2NHCH_2CH_2NHCH_2CH_2NH_2$.

5. A method for the manufacture of a topical pharmaceutically-active antimicrobial composition which comprises admixing a sterol conjugate compound of a formula selected from the group consisting of (A)

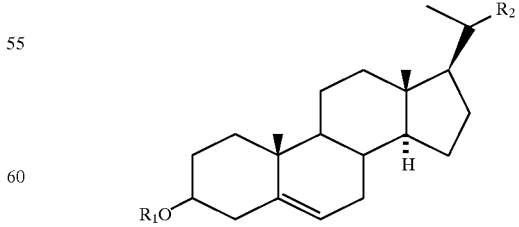

wherein $R_1$ is from the group H or $SO_3H$, and wherein $R_2$ is from the group CO-spermine, $CONHCH_2CH_2CH_2CH_2NH_2$, and $CONHCH_2CH_2NHCH_2CH_2NHCH_2CH_2NH_2$; (B)

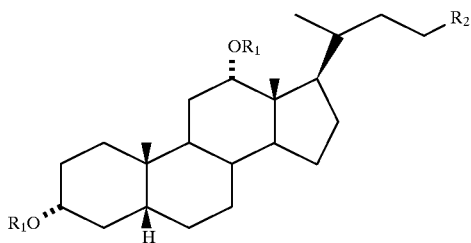

wherein $R_1$ is from the group H or $SO_3H$, and wherein $R_2$ is from the group CO-spermine, $CONHCH_2CH_2CH_2CH_2NH_2$, and $CONHCH_2CH_2NHCH_2CH_2NHCH_2CH_2NH_2$; (C)

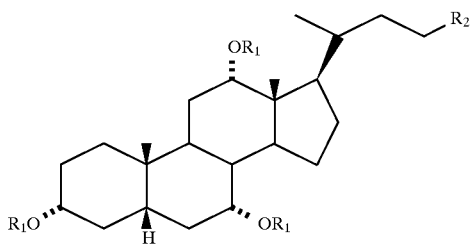

wherein $R_1$ is from the group H or $SO_3H$, and wherein $R_2$ is from the group CO-spermine, $CONHCH_2CH_2CH_2CH_2NH_2$, and $CONHCH_2CH_2NHCH_2CH_2NHCH_2CH_2NH_2$; (D)

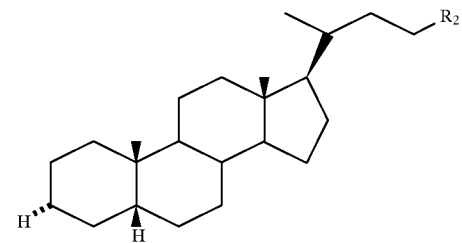

wherein $R_2$ is from the group CO-spermine, $CONHCH_2CH_2CH_2CH_2NH_2$, and $CONHCH_2CH_2NHCH_2CH_2NHCH_2CH_2NH_2$; (E)

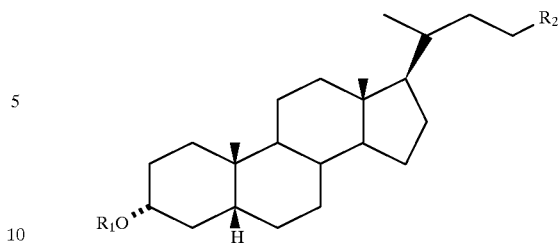

wherein $R_1$ is from the group H or $SO_3H$, and wherein $R_2$ is from the group CO-spermine, $CONHCH_2CH_2CH_2CH_2NH_2$, and $CONHCH_2CH_2NHCH_2CH_2NHCH_2CH_2NH_2$; (F)

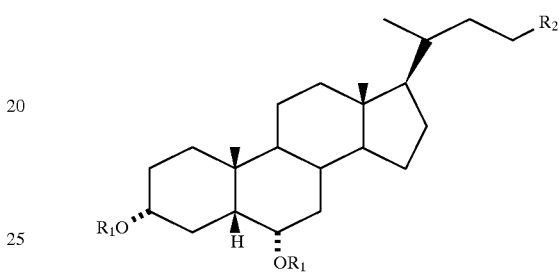

wherein $R_1$ is from the group H or $SO_3H$, and wherein $R_2$ is from the group CO-spermine, $CONHCH_2CH_2CH_2CH_2NH_2$, and $CONHCH_2CH_2NHCH_2CH_2NHCH_2CH_2NH_2$; and (G)

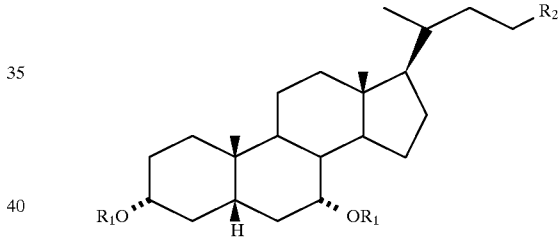

wherein $R_1$ is from the group H or $SO_3H$, and wherein $R_2$ is from the group CO-spermine, $CONHCH_2CH_2CH_2CH_2NH_2$, and $CONHCH_2CH_2NHCH_2CH_2NHCH_2CH_2NH_2$ with a pharmaceutically acceptable carrier for topical administration, said conjugate being in a sufficient concentration as to provide an antimicrobial dose of from 1 μg to 100 mg of said conjugate compound.

* * * * *